(12) United States Patent
Michaels et al.

(10) Patent No.: US 9,034,594 B2
(45) Date of Patent: May 19, 2015

(54) METHODOLOGY FOR VERIFYING CARBON STORAGE IN SEAWATER

(75) Inventors: Anthony Michaels, Palos Verdes Estates, CA (US); Sergio Sanudo-Wilhelmy, South Pasadena, CA (US); Douglas Capone, Rancho Palos Verdes, CA (US); James Moffett, South Pasadena, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1975 days.

(21) Appl. No.: 12/108,394

(22) Filed: Apr. 23, 2008

(65) Prior Publication Data

US 2008/0311611 A1 Dec. 18, 2008

Related U.S. Application Data

(60) Provisional application No. 60/913,868, filed on Apr. 25, 2007, provisional application No. 60/913,775, filed on Apr. 24, 2007.

(51) Int. Cl.
| | |
|---|---|
| *C12Q 1/02* | (2006.01) |
| *G06F 19/00* | (2011.01) |
| *G01N 31/00* | (2006.01) |
| *E21B 41/00* | (2006.01) |
| *C12Q 1/04* | (2006.01) |

(52) U.S. Cl.
CPC .............. *E21B 41/0064* (2013.01); *C12Q 1/04* (2013.01); *Y02C 10/14* (2013.01)

(58) Field of Classification Search
None
See application file for complete search history.

(56) References Cited

U.S. PATENT DOCUMENTS

| | | | |
|---|---|---|---|
| 5,535,701 A | 7/1996 | Markels | |
| 5,967,087 A | 10/1999 | Markels | |
| 6,056,919 A | 5/2000 | Markels | |
| 6,200,530 B1 | 3/2001 | Markels | |
| 6,408,792 B1 | 6/2002 | Markels | |
| 6,440,367 B2 * | 8/2002 | Markels, Jr. | 422/40 |
| 6,729,063 B1 | 5/2004 | Markels | |
| 7,975,651 B2 * | 7/2011 | Lutz | 119/215 |
| 2003/0012691 A1 * | 1/2003 | Markels, Jr. | 422/40 |
| 2007/0028848 A1 | 2/2007 | Lutz | |

* cited by examiner

*Primary Examiner* — Vera Afremova
(74) *Attorney, Agent, or Firm* — McDermott Will & Emery LLP

(57) ABSTRACT

A method for verifying carbon storage in seawater to which a growth stimulant has been supplied for stimulating a bloom of nitrogen fixing organisms for enhancing carbon storage therein, comprises selecting a region of seawater including a surface mixed layer, a euphotic zone extending below the surface mixed layer, and a plurality of deeper zones; determining the effect of growth stimulant on the rate of nitrogen fixation and carbon transport in the region; and determining the amount of carbon stored at different depths and projected duration of carbon storage at each of the depths.

14 Claims, No Drawings

METHODOLOGY FOR VERIFYING CARBON STORAGE IN SEAWATER

RELATED APPLICATIONS

This application claims the benefit of priority of U.S. Provisional Application Ser. No. 60/913,775, filed Apr. 24, 2007 and U.S. Provisional Application Ser. No. 60/913,868, filed Apr. 25, 2007, the contents of each are herein incorporated by reference in their entirety.

STATEMENT REGARDING FEDERALLY SPONSORED RESEARCH

This invention was made with government support under the NSF Grant Nos. OCE 99-81545 and OCE 99-81371, awarded by the National Science Foundation. The government has certain rights in the invention.

TECHNICAL FIELD

The present disclosure relates to methods for verifying storage of carbon-containing material in seawater. The disclosure enjoys particular utility in assessing efficacy and longevity of carbon storage in seawater to which at least one growth stimulant has been supplied for stimulating a bloom of nitrogen fixing organisms and enhancing carbon storage therein.

BACKGROUND

Earth's oceans contain one of the largest reservoirs of mobile carbon on the planet, i.e., >~38,000 gigatons (Gt) of inorganic carbon, which mobile carbon constantly exchanges with atmospheric carbon. The amount of exchange varies with the area of ocean, with some areas outgassing carbon at about 100 Gt/yr. and other areas taking up more than about 100 Gt carbon/yr. On average, the oceans take up a few more Gt/yr. than they emit, and as a consequence of this natural imbalance, the oceans have presently absorbed about one third of all the carbon dioxide ($CO_2$) which has been formed due to burning of fossil fuels.

While a portion of the carbon uptake by ocean waters results from purely physical-chemical mechanisms, i.e., a higher atmospheric $CO_2$ concentration increases the gradient (difference) between the ocean surface $CO_2$ concentration and the atmosphere thereby increasing net carbon uptake by the ocean, another portion of the carbon uptake is caused by the ocean biology. The latter carbon uptake mechanism is amenable to stimulation by human activity.

The amount of carbon present at the ocean surface is largely controlled by the balance between carbon which is "upwelled" to the surface from below and carbon which is removed from the surface by biological processes. One method or mechanism for altering the long-term balance between upwelled and removed ("sequestered") carbon and increasing carbon uptake by the oceans comprises stimulating the creation of organic (i.e., carbon-containing) matter by supplying marine plant species (phytoplankton) with nutrients necessary for growth. Over most of the oceans, available nitrogen usually constitutes the most severely limiting plant nutrient, primarily because growth of the existing marine plants consumes nearly the entire amount of biologically available reactive nitrogen (i.e., nitrate, nitrite, ammonia, urea, and organic nitrogen). While addition of more reactive nitrogen to the oceans will effect additional marine plant growth resulting in increased $CO_2$ uptake, it is not possible or practical to directly supply sufficient nitrogen-based fertilizer to the oceans due to the prohibitive cost and the enormous mass of fertilizer required.

An alternative mechanism for providing reactive nitrogen species necessary for growth of marine plants involves conversion of diatomic nitrogen gas ($N_2$) into organic nitrogen by certain organisms, e.g., photosynthetic bacteria, via a natural fertilization process which occurs in the upper, i.e., sunlit, ocean layer(s). This mechanism can be stimulated by addition of trace amounts of iron (Fe) and other minerals and chemical compounds which normally are limiting with respect to growth of the organisms. In practice, this mechanism shifts the partitioning of carbon between the oceans and the atmosphere until the thus formed reactive nitrogen (usually stored as nitrate) is converted back to $N_2$ gas via a complementary bacterial process termed "denitrification". The timescale for nitrogen fixation resulting from this process ranges from several decades to millennia. In addition to this mechanism, nitrogen fixation in some major ocean areas is limited by the availability of phosphate.

Stimulation of nitrogen fixation by iron and other minerals, as described above, forms a pathway for influencing natural oceanic systems to induce a net shift of carbon from the atmosphere to the ocean. As indicated supra, the premise is that stimulation of nitrogen-fixing marine organisms by addition of trace substances (e.g., metals such as iron) that are either lacking or present in insufficient amount will both increase the total amount of nitrate present in the ocean and reduce the amount of residual phosphate present in the surface waters in the portions of the ocean that contain very low amounts of nitrate while containing measurable phosphate. The net effect of the stimulation process would be to shift a measurable amount of carbon away from the ocean surface into the deeper sea. As a consequence, the carbon shift from the surface to deeper regions of the ocean will influence the ocean/atmosphere partitioning of carbon and cause $CO_2$ to either enter the oceans more quickly in the plant growth-stimulated locations or to leave (i.e., outgas from) the plant growth-stimulated locations, depending upon the natural direction of $CO_2$ flux (flow) in that location.

It is expected that carbon sequestered by the above mechanism will be retained in subsurface (i.e., deeper) strata of the oceans due to continually occurring natural marine biological processes. Thus, every time new nitrate, with its newly sequestered carbon, is returned to the illuminated surface waters, the new nitrate and newly sequestered carbon are taken up by the marine plants and returned to the deeper strata. The process will continue until the nutrients are upwelled in an area of incomplete nutrient use (i.e., high nutrient, low chlorophyll or "HNLC" regions) where iron depletion occurs before nitrate and/or phosphate depletion, or until that water passes through an area of low oxygen content where denitrifying bacteria selectively remove the nitrate. In the latter instances, subsequent upwelling no longer stimulates the same plant biology and the $CO_2$ is once again in solution at the ocean surface for an extended time period. The result is re-equilibration with the atmosphere, and as a consequence, the interval (longevity) of sequestration of extra carbon via stimulation of nitrogen fixing organisms is expected to depend upon the time scales of mixing and circulation, estimated to be in the range from about 20 years to millennia. A small fraction of the carbon is expected to remain sequestered in sedimentary deposits.

Generally, organic matter that leaves the vicinity of the ocean surface is consumed by organisms present in the underlying water column. Most organic matter is remineralized within a few hundred meters of the surface and is available for upwelling back to the surface within 1-10 years, whereas organic matter which sinks more deeply below the ocean surface remains there as inorganic carbon and nutrients for centuries to millennia, depending upon the depth and degree of ocean mixing. At a given time, the upwelled water contains a mix of recently remineralized nutrients and nutrients which remineralized centuries ago. If the average depth of remineralization increases, the upwelled water will for some interval thereafter have less nutrient available from recent pools and at a later interval have more nutrient as the deeper pools return to the surface. This phenomenon effectively results in storage of the carbon by placing more of it in older, slower-to-return water masses. The processes or factors which control remineralization interval scales are unknown, but they do vary naturally and may be amenable to manipulation. In an extreme case, if the organic matter can be caused to reach the ocean floor, it can become part of the geological pools, whereby carbon may be sequestered for very long intervals (e.g., millennia to millions of years).

Another mechanism for carbon sequestration involves increasing the carbon content ("carbon richness") of sinking organic matter. In most of the world's oceans, the carbon-to-nitrogen-to phosphorus (C:N:P) ratios are similar. Thus, when organic nitrogen is converted to nitrate, most of the carbon associated therewith is converted to inorganic carbon. When the nitrate-laden water is returned to the illuminated surface layer of the ocean, the carbon requirements of the plants can be satisfied by the carbon in the water without necessity for additional carbon to be supplied from the atmosphere. However, some carbon compounds are more carbon-rich than others and the stimulation of high carbon-nitrogen or carbon-phosphate plants is expected to increase the amount of carbon removed from the water. If this carbon is remineralized along with the nutrients, it will again be present in water returned to the surface and will remain therein only if the high C:N organic matter is reformed. Therefore, if this carbon is not re-used but stored as organic carbon or even buried, it will be effectively removed (sequestered) from the atmosphere for long time intervals. While the mechanisms that control the C:N and C:P ratios of sinking materials are unclear, variation thereof does occur naturally.

Inasmuch as the storage of anthropogenic carbon in ocean waters is currently of great interest as a potentially economically viable approach for addressing and mitigating the increasing problem of global warming attributed to the increasing content of greenhouse gases such as $CO_2$ in the earth's atmosphere, and in view of the foregoing, there exists a great need for improved methodology for quantitatively assessing and verifying the amount and predicted duration of carbon storage/sequestration afforded by stimulation of blooms of nitrogen fixing organisms. Accordingly, the present disclosure provides a comprehensive methodology for quantitative determination of the efficacy and predicted longevity of carbon sequestration in ocean waters afforded by nitrogen fixation.

SUMMARY

An advantage of the present disclosure is improved methodology for measuring and verifying carbon storage in seawater.

Another advantage of the present disclosure is improved methodology for measuring and assessing carbon storage in seawater resulting from stimulation of nitrogen fixing organisms.

Yet another advantage of the present disclosure is improved methodology for determining projected duration of carbon storage in seawater resulting from stimulation of nitrogen fixing organisms.

Additional advantages and other features of the present disclosure will be set forth in the description which follows and will become apparent to those having ordinary skill in the art upon examination of the following or may be learned from the practice of the present disclosure. The advantages of the present disclosure may be realized and obtained as particularly pointed out in the appended claims.

According to an aspect of the present disclosure, the foregoing and other advantages are obtained by an improved method for verifying carbon storage in a selected region of seawater to which a growth stimulant has been supplied for stimulating a bloom of nitrogen fixing organisms for enhancing carbon storage therein, comprising steps of:

(a) selecting a region of seawater including a surface mixed layer, a euphotic zone extending below the surface mixed layer, and a plurality of deeper zones;

(b) determining the effect of the growth stimulant on the rate of nitrogen fixation and carbon transport in the region; and (c) determining the amount of carbon stored at different depths of the region and projected duration of carbon storage at each of the depths.

According to embodiments of the present disclosure, step (a) comprises selecting the region based upon:

(i) presence of requisite amounts of selected nitrogen-containing species, soluble reactive phosphate and organic phosphorus, iron, and nitrogen fixing organisms in the surface mixed layer;

(ii) water temperature at or above a predetermined minimum value;

(iii) presence of mixed layers shallower than a predetermined depth;

(iv) presence of convergent eddies greater than a predetermined size; and (v) presence of subsurface conditions promoting carbon storage for predetermined durations.

In certain embodiments of the disclosure, the selected region satisfies a majority of the following criteria:

(i) concentrations of nitrate, nitrite, ammonia, and urea in the surface mixed layer are each $<\sim 0.1$ µmole/kg;

(ii) combined concentration of soluble reactive phosphate and organic phosphorus is $>\sim 0.2$ µmole/kg;

(iii) concentration of all iron species is $<\sim 1$ nanomole/kg;

(iv) nitrogen fixing organisms are present;

(v) surface mixed layers shallower than $\sim 50$ m;

(vi) water temperature $>\sim 20°$ C.;

(vii) presence of convergent eddies $>\sim 100$ km; and (viii) presence of subsurface conditions for promoting carbon storage via circulation.

In certain embodiments of the disclosure, step (a) further comprises:

(i) establishing treatment areas and control areas within the selected region;

(ii) determining initial profiles at randomly selected locations within the treatment areas and control areas, each of the profiles including measured values of total dissolved inorganic carbon, total organic carbon, all forms of nitrogen and phosphorus nutrients, dissolved oxygen, and iron; and (iii) deploying a plurality of calibrated surface tethered, free drifting, or neutral buoyant sediment traps at a plurality of predetermined depths within the treatment and control areas.

In certain embodiments, step (a) includes determining initial profiles for the mixed layer, the euphotic zone, and the plurality of deeper zones of each of the treatment and control areas.

In certain embodiments, the method further comprises supplying at least one growth stimulant, such as iron, to the treatment areas for stimulating the bloom of nitrogen fixing organisms therein.

In certain embodiments of the disclosure, step (b) comprises:

(i) determining post-bloom profiles at the selected locations within the treatment areas and control areas, each of the profiles including measured values of total dissolved inorganic carbon, total organic carbon, nitrogen and phosphorus nutrients, dissolved oxygen, and iron;

(ii) measuring $N^{15}$ of nitrate and suspended organic nitrogen at preselected depths of the selected locations within the treatment and control areas utilized in determining the initial profiles;

(iii) measuring total carbon, nitrogen, phosphorus, and $N^{15}$ in samples recovered from each of the sediment traps; and (iv) determining integrated flux of each of the measured quantities over the deployment period of the sediment traps.

In certain embodiments of the disclosure, step (c) comprises:

(i) determining mean values and variance of the data obtained from the treatment and control areas at each depth;

(ii) determining the time-point at which the differences between mean treatment and control profiles are greatest;

(iii) utilizing the reduction in total carbon integrated over the mixed layer for the above-determined time-point as a measure of instantaneous carbon storage;

(iv) determining an increase in total carbon below the surface of the selected region based upon a decrease in total carbon at the surface of the region;

(v) determining long term carbon storage from the difference between sediment trap fluxes at deeper depths of the treatment and control areas;

(vi) determining a probability density function of storage times for total carbon fixed by nitrogen fixing organisms based upon differences in carbon or sediment trap fluxes; and (vii) determining total nitrogen fixation rate on the basis of a comparison of $N^{15}$ content of the treatment and control areas for indicating remineralization of nitrogen from recently fixed nitrogen gas.

In certain embodiments of present disclosure, a computer system is provided. The computer system comprises one or more computer storage devices that have stored thereon one or more computer programs, one or more input devices configured to receive data, one or more processors configured to process the data under the control of one or more of the computer programs that is connected to the storage devices and the input devices, and one or more output devices that are connected to the processors and configured to deliver the results of the processing by the processors to a user.

The computer system is programmed to determine an amount of carbon stored at a plurality of different depths in selected regions of seawater. The selected region including a surface mixed layer, a euphotic zone below the surface mixed layer, and a plurality of deeper zones, where a growth stimulant has been supplied for stimulating a bloom of nitrogen fixing organisms for enhancing carbon storage therein. The computer system is also programmed to determine a projected duration of carbon storage at each of the plurality of different depths.

In certain embodiments of the present disclosure, a computer readable storage medium is provided. The computer readable storage medium contains a computer program configured to cause the following to occur when read and processed by a computer system: determination of an amount of carbon stored at a plurality of different depths in selected regions of seawater, the selected region including a surface mixed layer, a euphotic zone below the surface mixed layer, and a plurality of deeper zones, where a growth stimulant has been supplied for stimulating a bloom of nitrogen fixing organisms for enhancing carbon storage therein and projection of a duration of carbon storage at each of the depths.

Additional advantages and aspects of the present disclosure will become readily apparent to those skilled in the art from the following detailed description, wherein embodiments of the present disclosure are shown and described, simply by way of illustration of the best mode contemplated for practicing the present disclosure. As will be described, the present disclosure is capable of other and different embodiments, and its several details are susceptible of modification in various obvious respects, all without departing from the spirit of the present disclosure. Accordingly, this description is to be regarded as illustrative in nature, and not as limitative.

DETAILED DESCRIPTION

The present disclosure is based upon recognition that the stimulation of nitrogen fixation, e.g., by iron and other minerals contained in aeolian dust, represents a significant opportunity to influence natural ocean systems to induce a net shift of carbon from the atmosphere to the sea. The premise is that stimulation of nitrogen-fixing organisms by the addition of trace substances, e.g., metals such as iron, in which they are deficient, increases the total amount of nitrate in the ocean and draws down the residual phosphate in the surface waters of the portions of the oceans which contain very little nitrate but measurable phosphate. The net effect is a substantial and significant shift of carbon away from the surface into deeper regions of the oceans. The shift in the carbon content of the ocean surface in turn affects the ocean-atmosphere partitioning of carbon and causes $CO_2$ to either enter the ocean more quickly in treated locations or leave them more slowly, depending upon natural factors at the locations.

The carbon stored (sequestered) by this mechanism is expected be retained in the subsurface ocean by the continued natural activities of marine biology. Whenever fresh nitrate, with its "new" carbon, is returned to the illuminated surface waters, the plants in the sea take up both and return them to the deep sea. This process continues until those nutrients are upwelled in an area of incomplete nutrient use (i.e., the high nutrient, low chlorophyll "HNLC" regions) or until that water passes through a low oxygen area where denitrifying bacteria remove the nitrate. In such instances, subsequent upwelling no longer stimulates the same biology and the $CO_2$ is once again in solution for an extended period at the ocean surface, leading to re-equilibration with the atmosphere. Consequently, these mechanisms retain extra carbon in the ocean on the time-scales of mixing and circulation, estimated to be on the order of 20-1,000 years. Storage in sediments may afford some longer term storage, but this is expected to account for only a small proportion of the carbon.

As indicated supra, there exists a great need for improved methodology for quantitatively assessing and verifying the amount and predicted duration of carbon storage/sequestration afforded by stimulation of blooms of nitrogen fixing organisms. Accordingly, the present disclosure provides a comprehensive methodology for quantitative determination of the efficacy and predicted longevity of carbon sequestration in ocean waters afforded by nitrogen fixation.

According to certain embodiments of the present disclosure, a comparison of profiles of control areas of a selected region, i.e., areas not supplied with growth stimulant(s) for stimulating a bloom of nitrogen fixing organisms, with treatment areas of the selected region, i.e., areas supplied with growth stimulant(s) for stimulating a bloom of nitrogen fixing organisms, is expected to indicate a decline in dissolved inorganic carbon (DIC) at the ocean surface as well as an increase at subsurface depths. This phenomenon is utilized as a direct measure of carbon shift/m$^2$, and is scaled up to the extent of the treated area (bloom area).

Generally the $N^{15}$ content (where $N^{15}$ is the heavy isotope of nitrogen) of nitrate present in ocean water is about 5 permil (where "permil" is a standard measure of the concentration of stable isotopic tracers in seawater with reference to a fixed standard), whereas the $N^{15}$ content of organic nitrogen present due to nitrogen fixation is essentially 0 permil. Therefore, as new nitrate is added to a water column from the bloom of nitrogen fixing organisms, the average $N^{15}$ content of the nitrate profile changes. The observed $N^{15}$ shift is used for estimating the total amount of nitrate that originated from the bloom, which amount is taken as stoichiometrically related to the amount of carbon shifted from the surface to midwaters, i.e., those layers of water below the surface where organic nitrogen was converted back to nitrate. Carbon removed from the surface and reappearing at depth reflects the shifts in nitrogen multiplied by the observed carbon-to-nitrogen stoichiometry, usually 6.6 C to 1 N (the latter ratio generally being referred to as the "Redfield ratio"). This is a second measure of carbon sequestration, and also is a key indicator of carbon retention in the water as the new nitrate allows this carbon to be continuously returned to the deep sea each time it is returned to near the surface when used by marine plants in the presence of light.

$N^{15}$ measurements of the dissolved organic nitrogen ("DON") and particulate organic nitrogen ("PON") are representative of the presence of additional nutrient(s) created by the bloom, but not yet remineralized. This is matched by about 6.6 times as much carbon which, when present below the surface mixed layer, can also be considered as sequestered.

Phosphate profiles exhibit a stoichiometric pattern similar to the carbon, but at C:P ratios ranging from about 106:1 to greater than about 200:1. The removal of phosphate from the surface waters thereby provides a third measure of carbon sequestration and affords a measure of remaining available phosphate.

The iron profiles afforded by the methodology of the present disclosure provide an indication of the amount of residual iron not yet used by the organisms of the water column. These data, when combined with the phosphate data, indicate the potential for further nitrogen fixation and carbon sequestration beyond the validity measurement period. Using the stoichiometry observed up to the latter time, an estimate of future sequestration activity can be made, which sequestered carbon is additional to the measured sequestered carbon.

Carbon removed from the surface of the treatment areas is likely to have been sequestered with a higher C:N ratio than the average 6.6:1 ratio. However, as the nitrate is returned to the surface by mixing and re-use by regular plants, the latter will occur at a ratio near the 6.6:1 ratio. Consequently, the estimate of long-term carbon storage must be reduced so that it is limited to 6.6 times the amount of reactive nitrogen (i.e., nitrate, nitrite, ammonia, urea, DON, and PON) created in the treatment area.

More specifically, a method for verifying carbon storage in a selected region of seawater to which a growth stimulant has been supplied for stimulating a bloom of nitrogen fixing organisms for enhancing carbon storage therein, comprises the steps of:

(a) selecting a region of seawater including a surface mixed layer, a euphotic zone below the surface mixed layer, and a plurality of deeper zones;

(b) determining the effect of the growth stimulant on the rate of nitrogen fixation and carbon transport in the region; and (c) determining the amount of carbon stored at different depths of the region and projected duration of carbon storage at each of the depths.

Step (a) for selecting suitable region(s) for performing the instant verification method is based upon:

(i) presence of requisite amounts of selected nitrogen-containing species, soluble reactive phosphate and organic phosphorus, iron, and nitrogen fixing organisms present in the surface mixed layer of the region;

(ii) water temperature at or above a predetermined minimum value;

(iii) presence of mixed layers shallower than a predetermined depth;

(iv) presence of convergent eddies greater than a predetermined size; and (v) presence of subsurface conditions promoting carbon storage for predetermined durations.

In certain embodiments, the selected region satisfies a majority of the following criteria:

(i) concentrations of nitrate, nitrite, ammonia, and urea in the surface mixed layer are each <~0.1 mole/kg;

(ii) combined concentration of soluble reactive phosphate and organic phosphorus is >~0.2 μmole/kg;

(iii) concentration of all iron species is <~1 nanomole/kg;

(iv) presence of nitrogen fixing organisms with slow growth rate due to inadequate availability of iron, e.g., as indicated by the expression of iron stress proteins or other known physiological indicators of iron stress;

(v) surface mixed layers shallower than ~50 m;

(vi) water temperature >~20° C.;

(vii) presence of convergent eddies >~100 km; and (viii) presence of subsurface conditions for promoting carbon storage via circulation.

In certain embodiments, a general circulation model ("GCM") of the ocean, validated by ocean tracer data, is used for selecting regions having appropriate ventilation residence times at all depths, and a minimum depth should be defined at the selected region for each residence time, e.g., noting that at all ocean depths greater than about 550 m, greater than about 100 yrs. elapse before that water returns to ocean surface.

As for criterion (viii), subsurface conditions also promote carbon sequestration for defined time intervals by re-use of nutrients when circulation provides rapid mixing of the water back to the surface. Subsurface conditions may be ascertained by:

(i) using a tracer approach within a GCM;

(ii) fixing nitrogen gas to reactive nitrogen species (i.e., nitrate, nitrite, ammonia, urea, and organic nitrogen) and transporting same to predetermined depth(s) according to measured or estimated mineralization vs. depth profile;

(iii) following nutrient fates in multiple water parcels as the nutrient(s) are re-mixed to surface water, re-used, and re-transported to greater depth(s), and as they are transported horizontally and vertically via circulation and mixing;

(iv) measuring where the above cycle intercepts denitrification zones, followed by a final return to the surface or return to the surface in areas containing persistent excess nitrate (i.e., high nutrient, low chlorophyll HNLC areas);

(v) measuring the time interval between nitrogen fixation and return to the ocean surface; and (vi) calculating a probability density function for the interval required for return of water to the ocean surface at each location utilizing the data obtained in item (iv).

Region selection should also include confirmation that nitrogen fixing organisms are present but exhibit indications of starvation of the growth stimulants which are to be supplied (e.g., expressing genes for low iron metabolism or having low iron-to-organic matter ratios).

In certain embodiments, step (a) further includes the steps of:

(i) establishing treatment areas and control areas within the selected region;

(ii) determining initial profiles at randomly selected locations within the treatment areas and control areas, each of the profiles including measured values of total dissolved inorganic carbon, total organic carbon, all forms of nitrogen and phosphorus nutrients, dissolved oxygen, and iron; and (iii) deploying a plurality of calibrated surface tethered, free drifting, or neutral buoyant sediment traps at a plurality of predetermined depths within the treatment and control areas.

In certain embodiments of the disclosure, these steps comprise:

(i) defining at least one treatment area ("patch") of ocean to be treated with growth stimulant, as by deploying drogue buoys that move with the water;

(ii) defining at least one untreated control area by deploying drogue buoys that move with the water. The control area(s) preferably are of similar dimensions as the treatment area(s), and may be located either within a nearby eddy or away from the treatment area(s). The control areas are selected such that they represent similar waters in all respects to the treatment areas, except for the addition of the growth stimulant. A buffer zone of adequate size should exist between the treatment and control areas to minimize mixing therebetween.

In certain embodiments, the patch is centered in an eddy and the patch size is larger than 50 km by 50 km. In certain embodiments, the patch size is about 100 km by 100 km or greater. The growth stimulant can be added to the seawater within the patch by one or more ships. In certain embodiments, the one or more ships release the growth stimulant into the seawater at predetermined amount of growth stimulant per square kilometer. The amount of growth stimulant released is controlled to be sufficient to stimulate a bloom of nitrogen fixing organisms, but not to be toxic at the point of release before the growth stimulant diffuses throughout the mixed layer of the patch.

In certain embodiments, step (a) further includes a step of determining initial profiles for the mixed layer, euphotic zone, and plurality of deeper zones of each of the treatment and control areas.

In certain embodiments, a preliminary step of supplying at least one growth stimulant to the treatment areas for stimulating the bloom of nitrogen fixing organisms therein is performed. In certain embodiments, the growth stimulant contains iron in the form of ferrous sulfate.

The initial (or "time zero") profiles are determined at randomly selected locations with respect to the drogue locations within the treatment and control areas, and include measurement of the total dissolved inorganic carbon and total organic carbon, all forms of nitrogen and phosphorus nutrients, dissolved oxygen, and iron. In certain embodiments, each profile includes at least 4 samples within the mixed layer, at least 6 samples within the euphotic zone, and at least 4 samples between preselected depth zones of interest, and at least 4 samples below the deepest zone of interest.

By way of illustration only, assuming a mixed layer depth of 50 m, a euphotic zone depth of 100 m, a 50 yr. storage depth of 250 m, and a 100 yr. storage depth of 500 m, the samples would include: 4 at 0-50 m, at least 2 additional at 50-100 m, at least 4 at 100-250 m, at least 4 at 250-500 m, and at least 4 below 500 m.

Addition of iron and/or other growth stimulants to the treatment area(s) should be conducted such that the requisite time for stimulant addition is short relative to the anticipated interval for development of nitrogen fixation. In a certain embodiment, the requisite time for stimulant addition is about 2 wks.

As indicated supra, the sediment traps may be free drifting or neutral buoyant. In certain embodiments, the sediment traps are preferentially neutral buoyant. The sediment traps should be deployed at randomly selected locations at target depths determined by the modeling process used for measuring residence times of interest (e.g., a 50 yr. residence time at a 250 m depth). In certain embodiments, Thorium (Th) calibrations are performed on the traps positioned at shallower depths; a plurality of traps are deployed at the base of the euphotic zone for obtaining optimum calibration data and best comparison with carbon data; and recovery and redeployment of the traps at given locations are performed at periodic time intervals throughout development of the nitrogen fixation bloom.

In certain embodiments of the disclosure, step (b) comprises:

(i) determining post-bloom profiles at the selected locations within the treatment areas and control areas, each of the profiles including measured values of total dissolved inorganic carbon, total organic carbon, nitrogen and phosphorus nutrients, dissolved oxygen, and iron;

(ii) measuring $N^{15}$ of nitrate and suspended organic nitrogen at the preselected depths of the selected locations within the treatment and control areas utilized in determining initial profiles;

(iii) measuring total carbon, nitrogen, phosphorus, and $N^{15}$ in samples recovered from each of the sediment traps; and (iv) determining the integrated flux of each of the measured quantities over the deployment period of the sediment traps.

In certain embodiments, the surface characteristics of the bloom are observed and monitored to determine the point in time at which most of the nitrogen fixation has occurred and most of the organic carbon has been created and/or exported. This point in time can be about 2-3 months. In certain embodiments, surface measurements include basic parameters and direct measurement of nitrogen fixation.

In certain embodiments, one or more time-points are selected for performing post-bloom measurements. In certain embodiments, (i) the same number of sampling locations are used as in the initial ("time zero") measurements;

(ii) the same locations with respect to the drogues are used, with appropriate correction for any distortion of the patch;

(iii) the same parameters are measured in the same way at both the treatment and control areas;

(iv) $N^{15}$ of the nitrate and suspended organic nitrogen are measured at all depths;

(v) at each time-point, the sediment traps are recovered and relocated for a synoptic endpoint opportunity; and (vi) the total carbon, nitrogen, phosphorus, and $N^{15}$ of organic nitrogen in all sediment trap samples is measured and the data from each location summed over the full deployment intervals to calculate integrated flux values.

In certain embodiments of the disclosure, step (c) comprises:

(i) determining mean values and variance of the data obtained from the treatment and control areas at each depth;

(ii) determining the time-point at which the differences between mean treatment and control profiles are greatest;

(iii) utilizing the reduction in total carbon integrated over the mixed layer for the above-determined time-point as a measure of instantaneous carbon storage;

(iv) determining an increase in total carbon below the surface of the selected region based upon a decrease in total carbon at the surface of the region;

(v) determining long term carbon storage from the difference between sediment trap fluxes at deeper depths of the treatment and control areas;

(vi) determining a probability density function of storage times for total carbon fixed by nitrogen fixing organisms based upon differences in carbon or sediment trap fluxes; and (vii) determining total nitrogen fixation rate on the basis of a comparison of $N^{15}$ content of the treatment and control areas for indicating nitrogen remineralization of nitrogen from recently fixed nitrogen gas.

In certain embodiments of the disclosure, step (c) includes:

(i) determining a mean and variance of the data for the treatment and control areas for each depth range for each time-point;

(ii) applying a correction at later time-points if the initial (time-zero) data exhibits a significant difference between treatment and control areas;

(iii) examining the difference(s) between mean treatment area and mean control area profiles to determine a single time-point where the difference is most significant. In this regard, earlier profiles will exhibit a smaller difference because the post-bloom pattern is still developing, and later profiles also exhibit small differences because mixing tends to erase any differences. The largest observed difference provides the best indication of what is actually occurring. For the single time-point determined statistically significant reductions in total carbon integrated over the mixed layer constitute the most accurate determination of instantaneous carbon storage. Increases in total carbon below the surface should equal the reduction in the surface waters, but the differences may not be significant if the measured signal is spread over too large a depth range. It is believed that sediment trap fluxes at the base of the euphotic zone equal the change in integrated total carbon over that same depth range at that time-point; and sediment trap fluxes at greater depths constitute independent measures of carbon storage for periods longer than the residence time of waters at those depths. The signal is the difference between the mean values at the treatment and control locations. The probability density function of storage times for total carbon fixed by nitrogen fixing organisms is also determinable using the carbon differences or sediment trap fluxes and modeled estimates of the residence time based upon biological re-use of nutrients before denitrification or surfacing in HNLC areas. The $N^{15}$ content of nitrate below the treatment area(s) should be compared with the $N^{15}$ content of the control area(s). Reduction of $N^{15}$ content in nitrate indicates remineralization of nitrogen from recently fixed nitrogen gas and is an independent measure of the total nitrogen fixation rate. For example, if the nitrate is normally 5 permil and presently is 4.5 permil, it indicates that 10% of the nitrate from nitrogen fixation (dilution by nitrate with a value of 0 permil). If the total nitrate is 1 µmole/kg, then 0.1 mole/kg is remineralized by treatment with the growth stimulant. Also, integration of these values to depth should equal the estimate of total nitrogen fixation. Multiplying the total nitrogen fixation by 6.6 provides a close indication of the carbon reduction in the treatment area.

In the event of disagreement in results between methods, the hierarchy of measurement quality, from most to least accurate, is as follows:

(1) total carbon loss from the mixed layer or euphotic zone;
(2) sediment trap fluxes;
(3) $N^{15}$ of nitrate; and
(4) remineralization;

In this regard, large discrepancies indicate a poorly resolved carbon signal, whereas small discrepancies or large-scale agreement indicate a robust carbon signal.

Measurements of residual iron and phosphate can provide an estimate of amount of nitrogen fixation possible subsequent to the last sampling time-point. This additional carbon storage may be ascribed to the treatment process with lower confidence.

In certain embodiments, the amount of carbon stored and the duration of storage is determined during a verification cruise of the treated patch. The verification cruise can comprise one or more ships collecting necessary data, including seawater composition, within the treated patch. In certain embodiments, the robots or buoys collect the data and relay it to a ship or land-based data collection sites. The data can be relayed via satellite.

In certain embodiments of present disclosure, a computer system is provided. The computer system comprises one or more computer storage devices that have stored thereon one or more computer programs, one or more input devices configured to receive data, one or more processors configured to process the data under the control of one or more of the computer programs that is connected to the storage devices and the input devices, and one or more output devices that are connected to the processors and configured to deliver the results of the processing by the processors to a user.

The computer system is programmed to determine an amount of carbon stored at a plurality of different depths in selected regions of seawater. The selected region including a surface mixed layer, a euphotic zone below the surface mixed layer, and a plurality of deeper zones, where a growth stimulant has been supplied for stimulating a bloom of nitrogen fixing organisms for enhancing carbon storage therein. The computer system is also programmed to determine a projected duration of carbon storage at each of the plurality of different depths.

In certain embodiments, the computer system is further programmed to determine post-bloom profiles at the selected regions. Each of the profiles include measured values of total dissolved inorganic carbon, total organic carbon, nitrogen and phosphorus nutrients, dissolved oxygen, and iron. $N^{15}$ of nitrate and suspended organic nitrogen is measured at selected depths of selected locations within the treatment and control areas utilized in determining initial profiles. The total carbon, nitrogen, phosphorus, and $N^{15}$ in samples recovered from sediment traps deployed at the plurality of different depths is measured. An integrated flux is determined of each of the measured quantities over a deployment period of the sediment traps.

In certain embodiments, the computer system is further programmed to determine mean values and variance of data obtained from treatment and control areas at each depth. The time-point at which the differences between mean treatment and control profiles are greatest is determined. An amount of carbon storage using a reduction in total carbon integrated over the mixed layer for the above-determined time-point is determined. An increase in total carbon below the surface of the selected region is determined based upon a decrease in total carbon at the surface of the region. A long term carbon storage is determined from the difference between sediment trap fluxes at deeper depths of the treatment and control areas. A probability density function of storage times for total carbon fixed by nitrogen fixing organisms is determined based upon differences in carbon or sediment trap fluxes. A total nitrogen fixation rate is determined on the basis of a comparison of $N^{15}$ content of the treatment and control areas.

In certain embodiments, the computer system is programmed to determine initial profiles for the mixed layer, the euphotic zone, and the plurality of deeper zones of each of the treatment and control areas.

In certain embodiments, the computer storage devices include hard disk drives or flash memories; the input devices include keyboards, mice, displays, modems, or sensors; the output devices include displays, printers, or modems.

The computer system can be deployed on one or more ships that collect data during a verification cruise or a growth stimulant deployment cruise. The computer system can comprise buoys or robotic data collection devices. Alternatively, the computer system can comprise land-based computers in which the seawater data is relayed to the land-based computer from ships or buoys via satellite.

In certain embodiments, the computer system records the results on a computer readable medium. The computer readable medium can be any known computer readable medium including flash memories, magnetic disks, optical disks, magneto-optical disks, and magnetic tapes.

In certain embodiments of the present disclosure, a computer readable storage medium is provided. The computer readable storage medium contains a computer program configured to cause the following to occur when read and processed by a computer system: determination of an amount of carbon stored at a plurality of different depths in selected regions of seawater, the selected region including a surface mixed layer, a euphotic zone below the surface mixed layer, and a plurality of deeper zones, where a growth stimulant has been supplied for stimulating a bloom of nitrogen fixing organisms for enhancing carbon storage therein and projection of a duration of carbon storage at each of the depths.

In certain embodiments, the computer program is configured to further cause the following to occur when read and processed by the computer system: determination post-bloom profiles at the selected regions, each of the profiles including measured values of total dissolved inorganic carbon, total organic carbon, nitrogen and phosphorus nutrients, dissolved oxygen, and iron; measurement of $N^{15}$ of nitrate and suspended organic nitrogen at selected depths of the selected locations within treatment and control areas utilized in determining initial profiles; measurement of total carbon, nitrogen, phosphorus, and $N^{15}$ in samples recovered from sediment traps deployed at the plurality of different depths; and determination of an integrated flux of each of the measured quantities over a deployment period of the sediment traps.

In certain embodiments, the computer program is configured to further cause the following to occur when read and processed by the computer system: determination of mean values and variance of data obtained from treatment and control areas at each depth; determination of the time-point at which the differences between mean treatment and control profiles are greatest; determination of an amount of carbon storage using a reduction in total carbon integrated over the mixed layer for the above-determined time-point; determination of an increase in total carbon below the surface of the selected region based upon a decrease in total carbon at the surface of the region; determination of long term carbon storage from the difference between sediment trap fluxes at deeper depths of the treatment and control areas; determination of a probability density function of storage times for total carbon fixed by nitrogen fixing organisms based upon differences in carbon or sediment trap fluxes; and determination of a total nitrogen fixation rate on the basis of a comparison of N's content of the treatment and control areas.

In certain embodiments, the computer program is configured to further cause the following to occur when read and processed by the computer system: determination of initial profiles for the mixed layer, the euphotic zone, and the plurality of deeper zones of each of the treatment and control areas.

In certain embodiments, the computer readable storage medium the storage medium is selected from the group consisting of flash memories, magnetic disks, optical disks, magneto-optical disks, and magnetic tapes.

In summary, the present disclosure provides a comprehensive methodology for quantitatively assessing and verifying the amount and predicted duration of carbon storage/sequestration afforded by stimulation of blooms of nitrogen fixing organisms, advantageously utilizing readily available measurement technologies in an economically viable manner.

In the previous description, numerous specific details are set forth, such as specific materials, techniques, processes, structures, etc., in order to provide a better understanding of the present disclosure. However, the present disclosure can be practiced without resorting to the details specifically set forth herein. In other instances, well-known processing techniques and methodologies have not been described in order not to unnecessarily obscure the present disclosure.

Only certain embodiments of the present disclosure and but a few examples of its versatility are shown and described in the present disclosure. It is to be understood that the present disclosure is capable of use in various other combinations and environments and is susceptible of changes and/or modifications within the scope of the concept(s) as expressed herein.

What is claimed is:

1. A method for verifying carbon storage in a selected region of seawater to which a growth stimulant has been supplied for stimulating a bloom of nitrogen fixing organisms for enhancing carbon storage therein, comprising steps of:

selecting said region of seawater including a surface mixed layer, a euphotic zone extending below said surface mixed layer, and a plurality of deeper zones;

establishing treatment areas and control areas within the selected region;

deploying a plurality of calibrated surface tethered, free drifting, or neutral buoyant sediment traps at a plurality of predetermined depths within said treatment and control areas;

determining initial profiles at randomly selected locations within said treatment areas and control areas, each of said profiles including measured values of total dissolved inorganic carbon, total organic carbon, all forms of nitrogen and phosphorus nutrients, dissolved oxygen, and iron;

determining the effect of said growth stimulant on the rate of nitrogen fixation and carbon transport in said region; and determining the amount of carbon stored at different depths of said region and projected duration of carbon storage at each of said depths, wherein the step of determining the amount of carbon stored at different depths of said region and projected duration of carbon storage at each of said depth comprises:
(i) determining mean values and variance of the data obtained from said treatment and control areas at each depth;
(ii) determining the time-point at which the differences between mean treatment and control profiles are greatest;
(iii) utilizing the reduction in total carbon integrated over the mixed layer for the above-determined time-point as a measure of instantaneous carbon storage;
(iv) determining an increase in total carbon below the surface of said selected region based upon a decrease in total carbon at the surface of said region;
(v) determining long term carbon storage from the difference between sediment trap fluxes at deeper depths of said treatment and control areas;
(vi) determining a probability density function of storage times for total carbon fixed by nitrogen fixing organisms based upon differences in carbon or sediment trap fluxes; and
(vii) determining total nitrogen fixation rate on the basis of a comparison of $N^{15}$ content of said treatment and control areas for indicating remineralization of nitrogen from recently fixed nitrogen gas.

2. The method according to claim 1, wherein the step of selecting said region of seawater comprises selecting said region based upon:
(i) presence of requisite amounts of selected nitrogen-containing species, soluble reactive phosphate and organic phosphorus, iron, and nitrogen fixing organisms in said surface mixed layer;
(ii) water temperature at or above a predetermined minimum value;
(iii) presence of mixed layers shallower than a predetermined depth;
(iv) presence of convergent eddies greater than a predetermined size; and
(v) presence of subsurface conditions promoting carbon storage for predetermined durations.

3. The method according to claim 1, wherein the step of determining initial profiles at randomly selected locations within said treatment areas and control areas comprises determining initial profiles for said mixed layer, said euphotic zone, and said plurality of deeper zones of each of said treatment and control areas.

4. The method according to claim 1, further comprising:
a step of supplying at least one said growth stimulant to said treatment areas for stimulating said bloom of nitrogen fixing organisms therein.

5. The method according to claim 4, wherein:
said step of supplying at least one said growth stimulant comprises supplying iron as said at least one growth stimulant.

6. The method according to claim 1, wherein the step of determining the effect of said growth stimulant comprises:
(i) determining post-bloom profiles at said selected locations within said treatment areas and control areas, each of said profiles including measured values of total dissolved inorganic carbon, total organic carbon, nitrogen and phosphorus nutrients, dissolved oxygen, and iron;
(ii) measuring $N^-$ of nitrate and suspended organic nitrogen at preselected depths of said selected locations within said treatment and control areas utilized in determining initial profiles;
(iii) measuring total carbon, nitrogen, phosphorus, and $N^-$ in samples recovered from each of said sediment traps; and
(iv) determining integrated flux of each of the measured quantities over the deployment period of said sediment traps.

7. The method according to claim 1, wherein said selected region satisfies a majority of the following criteria:
(i) concentrations of nitrate, nitrite, ammonia, and urea in said surface mixed layer are each $<\sim 0.1$ µmole/kg;
(ii) combined concentration of soluble reactive phosphate and organic phosphorus is $>\sim 0.2$ µmole/kg;
(iii) concentration of all iron species is $<\sim 1$ nanomole/kg;
(iv) nitrogen fixing organisms are present;
(v) surface mixed layers shallower than $\sim 50$ m;
(vi) water temperature $>\sim 20°$ C.;
(vii) presence of convergent eddies $>\sim 100$ km; and
(viii) presence of subsurface conditions for promoting carbon storage via circulation.

8. A computer system comprising:
one or more computer storage devices that have stored thereon one or more computer programs;
one or more input devices configured to receive data;
one or more processors configured to process the data under the control of the one or more computer programs that are connected to the storage devices and the input devices;
one or more output devices that are connected to the processors and configured to deliver results of the processing by the processors to a user, wherein the computer system is programmed to
determine an amount of carbon stored at a plurality of different depths in selected regions of seawater, said selected region including a surface mixed layer, a euphotic zone below said surface mixed layer, and a plurality of deeper zones, where a growth stimulant has been supplied for stimulating a bloom of nitrogen fixing organisms for enhancing carbon storage therein and projected duration of carbon storage at each of said depths;
determine mean values and variance of the data obtained from said treatment and control areas at each depth;
determinine the time-point at which the differences between mean treatment and control profiles are greatest;
determine an amount of carbon storage using a reduction in total carbon integrated over the mixed layer for the above-determined time-point;
determine an increase in total carbon below the surface of said selected region based upon a decrease in total carbon at the surface of said region;
determine long term carbon storage from the difference between sediment trap fluxes at deeper depths of said treatment and control areas;
determine a probability density function of storage times for total carbon fixed by nitrogen fixing organisms based upon differences in carbon or sediment trap fluxes; and
determine total nitrogen fixation rate on the basis of a comparison of $N^{15}$ content of said treatment and control areas for indicating remineralization of nitrogen from recently fixed nitrogen gas; and
determine post-bloom profiles at said selected regions, each of said profiles including measured values of total dissolved inorganic carbon, total organic carbon, nitrogen and phosphorus nutrients, dissolved oxygen, and iron.

9. The computer system of claim 8, further programmed to:
measure $N^{15}$ of nitrate and suspended organic nitrogen at selected depths of said selected locations within treatment and control areas utilized in determining initial profiles;
measure total carbon, nitrogen, phosphorus, and $N^{15}$ in samples recovered from sediment traps deployed at said plurality of different depths; and
determine an integrated flux of each of the measured quantities over a deployment period of said sediment traps.

10. The computer system of claim 8, further programmed to:
determine initial profiles for said mixed layer, said euphotic zone, and said plurality of deeper zones of each of said treatment and control areas.

11. A computer readable storage medium containing a computer program configured to cause the following to occur when read and processed by a computer system:
determination of an amount of carbon stored at a plurality of different depths in selected regions of seawater, said selected region including a surface mixed layer, a euphotic zone below said surface mixed layer, and a plurality of deeper zones, where a growth stimulant has been supplied for stimulating a bloom of nitrogen fixing organisms for enhancing carbon storage therein and projection of a duration of carbon storage at each of said depths;
determination of mean values and variance of data obtained from treatment and control areas at each depth;
determination of the time-point at which the differences between mean treatment and control profiles are greatest;
determination of an amount of carbon storage using a reduction in total carbon integrated over the mixed layer for the above-determined time-point;
determination of an increase in total carbon below the surface of said selected region based upon a decrease in total carbon at the surface of said region;
determination of long term carbon storage from the difference between sediment trap fluxes at deeper depths of said treatment and control areas;
determination of a probability density function of storage times for total carbon fixed by nitrogen fixing organisms based upon differences in carbon or sediment trap fluxes; and
determination of a total nitrogen fixation rate on the basis of a comparison of $N^{15}$ content of said treatment and control areas; and
determination of post-bloom profiles at said selected regions, each of said profiles including measured values of total dissolved inorganic carbon, total organic carbon, nitrogen and phosphorus nutrients, dissolved oxygen, and iron.

12. The computer readable storage medium of claim 11, wherein the computer program is configured to further cause the following to occur when read and processed by the computer system:
measurement of $N^{15}$ of nitrate and suspended organic nitrogen at selected depths of said selected locations within treatment and control areas utilized in determining initial profiles;
measurement of total carbon, nitrogen, phosphorus, and $N^{15}$ in samples recovered from sediment traps deployed at said plurality of different depths; and
determination of an integrated flux of each of the measured quantities over a deployment period of said sediment traps.

13. The computer readable storage medium of claim 12, wherein the computer program is configured to further cause the following to occur when read and processed by the computer system:
determination of initial profiles for said mixed layer, said euphotic zone, and said plurality of deeper zones of each of said treatment and control areas.

14. The computer readable storage medium of claim 11, wherein the wherein the storage medium is selected from the group consisting of flash memories, magnetic disks, optical disks, magneto-optical disks, and magnetic tapes.

* * * * *